United States Patent [19]

Dodd et al.

[11] Patent Number: 4,946,678

[45] Date of Patent: Aug. 7, 1990

[54] PROCESS OF TREATING THE SCALP AND HAIR

[76] Inventors: Thomas L. Dodd, Rt. 14, Box 733, Tyler, Tex. 75710; David A. O'Steen, 3601 Glendale Dr., Tyler, Tex. 75701

[21] Appl. No.: 346,885

[22] Filed: May 3, 1989

Related U.S. Application Data

[63] Continuation-in-part of Ser. No. 176,593, Apr. 1, 1988, abandoned.

[51] Int. Cl.$^5$ .................... A61K 35/54; A61K 37/02; A61K 31/19; A61K 31/17
[52] U.S. Cl. ..................................... 424/581; 424/70; 514/21; 514/568; 514/714
[58] Field of Search .................... 424/70, 95; 514/864, 514/880, 859, 2, 21

Primary Examiner—Jacqueline Stone
Assistant Examiner—Jean Witz
Attorney, Agent, or Firm—William E. Mouzavires

[57] ABSTRACT

A process and nourishing agent for treating and nourishing the scalp and hair to promote conditions for the natural growth of hair on a human head for the reversal of male pattern baldness in individual cases. The process includes the steps of cleansing the scalp and hair, opening the pores and follicles in the scalp and softening and removing clogging deposits from the pores and hair follicles, and then applying to the scalp a nourishing agent comprising a mixture of chalaza extracted from chicken eggs, unflavored powdered gelatin, and aqueous saline solution. In the preferred form of the invention, the pores of the scalp and hair follicles are opened and sanitized by repeated applications of a benzoic acid mixture and heat, and the clogging deposits and foreign matter are softened and separated by the application of a carbamide peroxide solution and heat. In addition, the balding area is massaged and oxygen is applied to the balding area to further assist opening of the pores and follicles and to stimulate blood circulation. After the scalp and hair follicles are prepared in the foregoing manner, the chalaza mixture is applied together with warm, moist pulsating oxygen to nourish and stimulate the hair roots and papillae.

11 Claims, No Drawings

PROCESS OF TREATING THE SCALP AND HAIR

RELATED APPLICATION

The present application is a continuation-in-part of our copending patent application Ser. No. 176,593, filed Apr. 1, 1988, and now abandoned.

FIELD OF THE INVENTION

The present invention generally relates to processes or methods of treating and nourishing the scalp and hair to promote conditions for the growth of human hair in male pattern baldness and to nourishing agents used therein to nourish and stimulate the roots and papillae of the hair and scalp. Included herein is a process for removing harmful clogging deposits from the pores of the scalp and hair follicles to open the same to permit the roots of the hair and papillae to receive nourishment to promote conditions for the growth of hair in cases of male pattern baldness.

BACKGROUND OF INVENTION

The loss of human terminal scalp hair leading to partial or complete male pattern baldness of the scalp has been of some concern to humanity through much of recorded history, as have efforts to restore the growth of hair. The growth of human terminal scalp hair, as distinguished from soft, wispy villous hair, is generally understood to involve three distinct phases: the anagen phase, in which the hair follicle is fully active and hair growth occurs, the catagen phase, a transitional phase in which growth slows and stops, and the telogen phase, during which the hair follicle is inactive and hair growth does not occur. Normally, the pattern of growth is cyclic, and the telogen phase is followed by a return to the anagen phase in which growth of the hair is again initiated. However, in some instances the cyclic pattern of growth is interrupted, resulting in premature baldness or male pattern baldness.

It is believed that the cessation of terminal hair growth is generally influenced and determined by three factors: nutrition, the level of sex hormones, particularly androgen, and hereditary or genetic factors The mechanism or mechanisms through which these factors influence interruption of the normal terminal scalp hair growth pattern is, however, not well understood. Other factors believed to be involved in premature loss of terminal scalp hair include poor blood circulation to the affected area, lack of necessary stimulation, and incomplete or improper nourishment of the hair root components.

Several approaches to correction of male pattern baldness have been attempted, with varying degrees of success. Transplantation of actively growing hair follicles and roots to the affected area has been successful in replacing at least a portion of the hair that has been lost.

Other approaches have attempted to address the problem of male pattern balding more directly, by inducing the growth of hair from existing follicles and roots. Those approaches include the use of vitamins and other dietary supplements, and the application of various types of preparations to the affected areas of the scalp. However, no treatment method known in the prior art has been totally successful in reversing the loss of human terminal scalp hair in male pattern baldness, and the general perception in the art has been that there is no effective means of treatment available.

OBJECTS OF THE PRESENT INVENTION

It is an object of the present invention to provide a novel process for treating and nourishing the scalp and hair to promote conditions for hair growth in individual cases of male pattern baldness and which process is both safe and effective and may be utilized at a relatively economical cost. It is a further object of the invention to provide a novel nourishing agent for use in the process of the invention to locally nourish the hair follicles, roots and papillae of the scalp.

A further object of the present invention is to provide a novel process of removing harmful, clogging deposits from the pores of the scalp and hair follicles to open the same to permit nourishment of the hair roots and papillae so as to promote conditions for the growth of hair in individual cases of male pattern baldness. Included herein is the provision in such a process of compositions and steps which are safe and effective and may be easily implemented without any special skill and with preparations readily available on the market.

A still further object of the present invention is to provide a process for unclogging the pores and hair follicles and providing nourishment to the roots and papillae of the hair in balding areas of human scalps suffering from male pattern baldness.

SUMMARY OF THE INVENTION

In its preferred form, the process of the present invention in summary comprises the steps of thoroughly cleansing the balding scalp area and softening and removing clogging deposits from the skin surface, skin pores, and hair follicles in the affected area of the scalp experiencing male pattern baldness; treating the affected area to open the pores and hair follicles and stimulate blood circulation to allow nourishment to reach the hair roots and papillae; applying directly to the scalp, slightly pressurized warm, moist gaseous oxygen to further open the pores and follicles and supply a sufficiency of oxygen to the hair roots and papillae; and applying to the balding area a nourishing agent comprising a natural protein mixture of chalaza extracted from chicken eggs, unflavored powered gelatin, and an aqueous saline solution. In conjunction with or immediately after the latter step, slightly pressurized, warm, moist gaseous oxygen is applied to the balding area and mixes with the nourishing agent to further stimulate and carry the nourishment to the hair follicles, roots and papillae. The scalp is then thoroughly rinsed with water to conclude one treatment.

It is typically necessary to repeat this procedure to obtain hair growth results and the preferred frequency is two to three times weekly for a period of time which varies from individual to individual and is preferably six months and at a minimum four months.

In the preferred process of the invention, a benzoic acid solution is applied at several stages to the balding area to open and sanitize the pores and hair follicles. Additionally, the balding area may be massaged to assist the opening of the pores and follicles. Furthermore, in the preferred process of the invention, carbamide peroxide is applied and massaged into the balding area and heat is also applied thereto in order to soften and separate the clogging deposits in the pores and follicles of the scalp.

A more detailed description of the steps of the process of the invention and of the composition of the agents used in the process of the invention, including the chalaza mixture nourishing agent of the invention, will now be described in more detail, along with representative examples of its use.

DETAILED DESCRIPTION OF THE INVENTION

The process of the present invention is used to soften and remove deposits which block the pores and hair follicles in balding areas of human scalps effected by male pattern baldness, and to then nourish the roots and papillae of the hair by introducing into the opened pores and follicles, a nourishing agent comprising a chalaza mixture to be specified below and warm, moist pulsating oxygen. A process in accordance with the preferred form of the invention includes the following sequential steps:

1. The scalp and hair are cleaned with a mild pH balanced shampoo, no conditioner is used.

2. The balding area is sprayed with a special benzoic acid mixture. The area is misted in sufficient quantity to thoroughly wet the scalp without excessive run-off.

The benzoic acid mixture contents are as follows:
1.0 percent benzoic acid in distilled water.
¼ teaspoon benzoic acid crystal per 1 gallon of distilled water to produce 1 percent concentration.

3. The subject's head is placed under an electric heat cap, which covers at least the balding scalp area, for three minutes. The purpose of steps 2 and 3 is to open and sanitize the pores and hair follicles of the scalp.

4. The heat cap is removed and the benzoic acid solution is removed with a warm towel dampened with water.

5. Carbamide peroxide (also known as urea hydrogen peroxide) paste is applied to the balding area, through any convenient means of application, in sufficient quantity to thoroughly wet the scalp without excessive run-off. The carbamide peroxide is massaged into the scalp for approximately sixty seconds. While it is preferred to use 12 percent solution of carbamide peroxide in water (readily available over-the-counter), other concentrations ranging from 8.0 to 20.0 percent may also be used.

6. The subject's head is placed under an electric heat cap for eight to ten minutes. This softens and separates deposits of sebum, the male hormones androgen and testosterone, and foreign matter in the pores and hair follicles of the scalp.

7. The heat cap is removed and the scalp rinsed thoroughly with warm water.

8. The scalp is towel dried. The balding area is again misted with the benzoic acid mixture described above.

9. The balding area is massaged with an electric hand vibrator for three minutes. This is to further open the pores and hair follicles of the scalp and stimulate blood circulation in the scalp.

10. The balding area is again misted with benzoic acid in the same concentration as used in the above steps.

11. The subject's head is placed under a specially designed oxygen cap. Pulsating at a rate of three seconds on and one second off, oxygen (100%) is warmed through a heated humidifier (105 degrees Fahrenheit) at 12 to 14 psi. This oxygen is applied directly to the scalp for five minutes. This will further open the pores and hair follicles of the scalp to allow the oxygen to penetrate to the roots and papillae of the hair follicles for stimulation and nourishment.

12. The cap is removed and the scalp is wiped with a damp, warm towel.

13. A nourishing agent, a chalaza protein mixture, is applied by any convenient means to the balding area in sufficient quantity to cover the area to be treated. Chalaza itself may be defined as either of a pair of spiral bands in the white of a bird's egg that extend from the yoke and attach to opposite ends of the lining membrane.

The following chalaza mixture is used and will provide enough product to conduct approximately 4 treatments:
Chicken egg chalaza from 6 eggs
2 ounces of normal saline solution
¼ teaspoon unflavored powered gelatin (for example, Hormel "Flavorset Gelatin")

14. In conjunction with or right after the application of the chalaza mixture, warm, moist, pulsating oxygen is applied to the balding area by way of a special hand held applicator for eight to ten minutes. This applicator provides pulsating (three seconds on and one second off) 100% oxygen warmed through a heated humidifier (105 degrees Fahrenheit) at 12 to 14 psi. The oxygen mixes with the chalaza mixture and carries the proteins into the hair follicles to nourish and stimulate the hair roots and papillae.

15. The scalp is then rinsed thoroughly with warm water. This concludes one treatment.

It is necessary to repeat this procedure to obtain hair growth results in individual cases of male pattern baldness. The preferred frequency is two to three times weekly for a period of time which varies from individual to individual and is preferably six months and at a minimum, four months. The number of treatments necessary to promote restoration of the hair growth pattern has been found to be highly individualized and the process is not effective in all cases. However, the success rate experienced by the inventors is approximately sixty percent. It is important that the chalaza based protein nourishing agent be used along with the other steps in the procedure and with the application of warm, moist, pulsating oxygen.

Although not absolutely certain, Applicants believe, based on experiments, that the effectiveness of their process in individual cases of male pattern baldness derives from opening and thorough cleansing the pores and hair follicles, stimulation of the scalp to increase the blood supply to the balding area and to the papilla of each hair follicle in the balding area, and localized nourishment of the roots and papilla of the hair follicles with the chalaza mixture and oxygen.

Case histories illustrative of the use and effectiveness of this invention are listed below.

EXAMPLE I

J. Mauldin
Mineola, Tex.

This process was used on a fifty year old male subject who was experiencing thinning of scalp hair from the crown of the head forward over the top of the head toward the hairline, with a bald area at the crown of the head in a generally circular pattern approximately two and one-half inches in diameter. In addition, the subject was experiencing progressive hair loss from the forehead toward the crown of the head in a receding hairline pattern. The cause of this condition was believed to be male pattern baldness and radiation treatments undergone by the subject. After two months of treatments in accordance with the present invention described above, three treatments per week, restoration of hair growth had become apparent The previously bald area at the crown of the head had become covered with permanent hair. Growth of hair through the thinning area at the top of the head had begun to manifest, and growth of hair in the receding hairline was increasingly evident and both growths continued with the treatment over six months.

EXAMPLE II

C. D. Hauser
Tyler, Tex.

The subject is a thirty-six year old male who was experiencing male pattern baldness—progressive thinning of scalp hair over the top of the head, with some bald patches in that area. The subject also exhibited a patch of fuzzy villous-type hair in an approximately one fourth inch band immediately forward of a bald area at the crown of the head. He had previously used the monoxidal product but was unsuccessful in growing hair on his head with this product. After two months of treatment, in accordance with the invention, with a treatment frequency of three times per week, the thinning of the subject's hair through the top and crown had been reversed, with a noticeable thickening of the hair in the affected areas. Hair growth in the patch or band previously exhibiting villous-type hair had progressed sufficiently to produce actively growing hair extending approximately one inch above the scalp. After six months of treatment in accordance with the invention, the crown or back of his head was covered with new hair, and the top center of his head had an appreciable amount of hair growth. Long terminal hair on the front hairline area replaced the previous villous hair.

EXAMPLE III

R. Boyd
Tyler Tex.

The subject is a thirty-four year old male who was experiencing male pattern baldness. He was 80 percent bald on the top of his head. After two months, two treatments per week in accordance with the present invention, substantial hair growth had begun in the crown and hair growth was visible in the front of the head.

EXAMPLE IV

R. Bradley
Corpus Christi, Tex.

The subject is a fifty-one year old male who was 90 percent bald on the top of his head due to male pattern baldness. His scalp hair started thinning in his early thirties and by age thirty-five, his scalp hair was sparse. He tried several different hair growth preparations including New Generation and Nutriol without success after twelve treatments in accordance with the invention over four weeks at three treatments per week, hair growth was apparent. After six months of treatments at a frequency of two treatments per week, there was substantial hair growth over the entire top of the head.

EXAMPLE V

M. Bockman
Mineola, Tex.

The subject is a forty-six year old male who was experiencing male pattern baldness and was almost completely bald through the top of the head. After twenty-four treatments in accordance with the invention over a four month period, hair growth was evidenced.

The following are cases of male pattern baldness where the process described above was used but where the nourishing agent did not contain the chalaza protein agent.

EXAMPLE VI

Buddy Dawson
Tyler, Tex.

The subject, age fifty-four, had a history of male pattern baldness since 1965 and had undergone various scalp treatments but without success in reversing the male pattern baldness. In Sep. 1987, the subject began treatments in accordance with the process described above except for the addition of the chalaza protein in the nourishing agent. The subject received three to four treatments per week over a course of at least three months but no new hair growth was seen to result in the male pattern balding area.

EXAMPLE VII

Ricky McPhearson
Tyler, Tex.

The subject, age 32, had a history of male pattern baldness starting in his early twenties and had undergone many hair growth "remedies" with no success in reversing loss of hair. In January 1988, the subject began treatments in accordance with the process described above except for the addition of the chalaza protein in the nourishing agent. The subject received treatments several times per week over the course of seven months and then dropped out of the treatment program when no new hair growth was seen to result in the male pattern balding area.

Applicants' verify believe that the process of the present invention will not only open and cleanse the pores and follicles to place the scalp in a healthy state but it will also nourish the hair roots and papillae to promote, in individual cases of male pattern baldness, restoration of hair growth in the balding areas.

Although a preferred process of the invention has been described above, it will be apparent to those skilled in the art that certain variations or modifications of the invention may also be used with effective results but without departing from the scope of the invention which is defined in the claims to follow.

What is claimed is:

1. A process of treating human scalp and hair comprising the steps of:
    applying a sanitizing agent to the balding area of the scalp to open and sanitize the pores and hair follicles of the scalp;
    applying heat and a softening agent to soften and separate sebum deposits in the pores and follicles of the scalp once they have been opened by the application of the sanitizing agent;
    then rinsing the scalp to remove deposits and agents previously applied thereto; and
    then applying a chalaza mixture and oxygen to the scalp to nourish the roots and papillae of the hair in the scalp.

2. The process defined in claim 1 wherein said chalaza mixture includes chalaza from chicken eggs, saline solution and gelatin.

3. The process defined in claim 2 wherein the oxygen is warm, moist oxygen and is applied at a pulsating rate for at least about eight minutes.

4. The process defined in claim 1 wherein the oxygen is warm, moist oxygen and is applied at a pulsating rate for at least about eight minutes.

5. The process defined in claim 1 wherein the sanitizing agent is applied before and after the application of the softening agent.

6. The process defined in claim 1 wherein warm, moist oxygen is applied to the scalp after the application of the softening agent and before the application of the chalaza mixture.

7. The process defined in claim 6 wherein the scalp is massaged after the application of the softening agent and prior to the application of the chalaza mixture.

8. The process defined in claim 6 wherein the sanitizing agent is applied to the scalp a number of times before and after the application of the softening agent and prior to the application of the chalaza mixture.

9. A process of treating human scalp and hair comprising the steps of applying a chalaza mixture in opened pores and follicles of the hair in the balding area of the scalp and applying oxygen to the balding area of the scalp.

10. The process defined in claim 9 wherein the chalaza mixture includes chicken egg chalaza, saline solution and gelatin.

11. The process defined in claim 9 wherein the oxygen is warm, moist oxygen and is applied at a pulsating rate for at least about eight minutes.

* * * * *